United States Patent [19]

Ahmad et al.

[11] Patent Number: 5,885,591
[45] Date of Patent: Mar. 23, 1999

[54] PERSONAL LUBRICANT COMPOSITIONS

[75] Inventors: Nawaz Ahmad, Monmouth Junction; Gregory E. Koll, Waldwick; Shun Y. Lin; Rohinton Toddywala, both of Plainsboro; Lorraine Wearley, Westfield, all of N.J.

[73] Assignee: Johnson & Johnson Consumer Products, Inc., Skillman, N.J.

[21] Appl. No.: 865,304

[22] Filed: May 29, 1997

Related U.S. Application Data

[60] Provisional application No. 60/021,042, Jul. 2, 1996.
[51] Int. Cl.$^6$ .................................................. A61K 9/00
[52] U.S. Cl. .................... 424/400; 514/944; 514/841; 424/DIG. 14; 424/401
[58] Field of Search .............. 424/401, DIG. 14, 424/400; 514/944, 841

[56] References Cited

U.S. PATENT DOCUMENTS

| | | |
|---|---|---|
| 4,482,537 | 11/1984 | El-Menshawy et al. . |
| 4,851,434 | 7/1989 | Deckner . |
| 4,952,560 | 8/1990 | Kigasawa et al. . |
| 4,983,379 | 1/1991 | Schaeffer . |
| 5,425,938 | 6/1995 | Znaiden et al. . |

OTHER PUBLICATIONS

Astroglide* personal lubricant label.

*Primary Examiner*—Thurman K. Page
*Assistant Examiner*—Brian K. Seidleck
*Attorney, Agent, or Firm*—Andrea L. Colby

[57] ABSTRACT

This invention relates to personal lubricant compositions that are at least between three and eighteen times more lubricious than the compositions known previously. The compositions of this invention contain one or more polyhydric alcohols, one or more water-soluble polymers derived from cellulose, water and, optionally, preservatives and alkali metal or alkaline earth metal bases. The compositions of this invention can provide a vehicle for delivering medicaments for contraception and for the treatment and prevention of disease. This invention also relates to methods of using the personal lubricant compositions of this invention.

3 Claims, 2 Drawing Sheets

PERSONAL LUBRICANT COMPOSITIONS

This application claims the benefit of U.S. Provisional Application No. 60/021,042, filed Jul. 2, 1996.

BACKGROUND OF THE INVENTION

FIELD OF THE INVENTION

This invention relates to personal lubricant compositions. They are at least between three and eighteen times more lubricious than the compositions known previously. The compositions of this invention can provide a vehicle for delivering medicaments for contraception and for the treatment and prevention of disease. This invention also relates to methods of maling and testing the personal lubricant compositions of this invention.

SUMMARY OF THE INVENTION

This invention relates to personal lubricant compositions. The compositions of this invention are pourable liquids or pourable low viscosity thixotropic gels which adhere to the mucous membranes and provide or add lubricity to these membranes such the oral, rectal or vaginal mucosa. Furthermore, the compositions of this invention, while lubricious, are not readily washed off the mucosal membranes. It is believed that the high lubricity of the compositions of this invention are due to the novel ratios between the elements of the compositions. By making compositions within the scope of this invention, surprisingly high lubricity values have been achieved.

The compositions of this invention preferably contain at least one water soluble polyhydric alcohol a water-soluble polymer derived from cellulose and water. The water-soluble polyhydric alcohol serves to increase the lubriciousness of the compositions. The water-soluble cellulose-derived polymer serves to impart the desired slipperiness and viscosity to the composition. Water is desired in sufficient quantity to provide consistency and viscosity to the composition.

The pH of the compositions of this invention should be adjusted to be compatible with the pH of the biomembrane to which they will be delivered. An inorganic base may be used to adjust the pH. The quantity of water in the compositions may also be adjusted in order to achieve the appropriate pH.

DETAILED DESCRIPTION OF THE PREFERRED EMBODIMENTS

Figure 1:
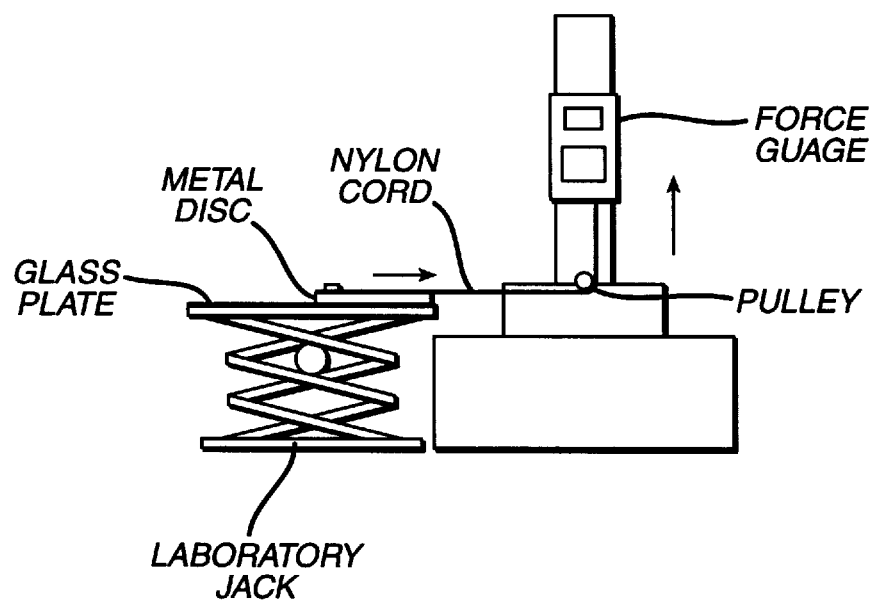
FIG. 1 is a frontal view of a device used to test coefficient of friction.

Preferably, the compositions of this invention contain at least one polyhydric alcohol which is water-soluble, a water-soluble polymer derived from cellulose and water, The water-soluble polyhydric alcohol portion of the compositions may contain one or more polyhydric alcohols. Preferably, the polyhydric alcohol portion should contain glycerin, propylene glycol, sorbitol or a combination thereof. Of course, other polyhydric alcohols known to those of ordinary skill in the art may be used in the products of this invention, such as, for example, polyethylene glycol ranging from molecular weight of from about 300 to about 1450.

The polyhydric alcohol portion of the product should make up from about 5 to about 90% by weight of the composition. More preferably, the compositions of this invention should contain a combination of two or more polyhdyric alcohols and one or more cellulose gums. Most preferably, the polyhydric alcohol portion of the composition should contain glycerin, propylene glycol and/or sorbitol in combination. Preferably, there should be from about 5 to about 50% by weight of glycerin and from about 2 to about 40% by weight of propylene glycol. Preferably, sorbitol is also used in the compositions and can range from about 5% to about 20% by weight of the composition.

The compositions of this invention should also contain one or more water-soluble cellulose-derived polymers. The polyol is preferably cellulose gum such as hydroxyethylcellulose, although other polyols known to those of ordinary skill in the art may be used, such as carboxyboxymethylcellulose, hydroxypropylcellulose and hydroxypropylmethylcellulose and the like. Preferably, a combination of gums and one of the polyhydric alcohols should be used, with one element being present in a significantly greater amount (polyhydric alcohol) than the other (cellulose gum). More preferably, the polyhydric alcohol is glycerin. Preferably, the gum is hydroxyethylcellulose.

It should be noted that raising the cellulose gum level decreases lubricity of the compositions. There is an optimum concentration of cellulose gum that imparts lubricity. Increasing the cellulose gum concentration increases or results in increase in the viscosity of the composition which increases the coefficient of friction and thereby decreases the lubricity. The polyol should be present in the compositions of this invention in the amount of from about 5 to about 30% A by weight of the composition. The gum should be present in the compositions of this invention in the amount of from about 0.1% to about 2% by weight of the composition. More preferably, it should be present in the amount of from about 0.25% to about 1%.

An inorganic base may be used to adjust the pH of the composition to be compatible with the vaginal rectal or oral membranes. Potassium hydroxide or another alkali metal or alkaline earth metal base may be useful to provide the appropriate pH. Of course, any other physiological acceptable base may also be utilized in this manner. From about 0.05 to about 5% by weight inorganic base is preferably used.

A preservative may be important for use in the products of this invention, in order to preserve the stability of the compositions of this invention and to prevent the growth of microorganisms therein. The preservative portion of the compositions of this invention may be one or more known preservatives, such as methylparaben, benzoic acid, sorbic acid, gallic acid or propylparaben. From about 0.05% to about 0.75% by weight preservative should be used.

Water functions to provide the appropriate pH consistency and viscosity to the composition.

The compositions of this invention may also be used to convey medication or other treatment agents to the biomembranes, such as contraceptives, antimicrobial agents and the like. Contraceptives may include nonoxynol-9, octoxynol-9 and menfegol. Antifungal agents include imidazole compounds such as miconazole, econazole, terconazole, saperconazole, itraconazole, butaconazole, clotrunzole, tioconazole and ketoconazole and the like. Antibacterial agents may also be present such as metronidazole, chlorhexidine gluconate and hydrogen peroxide. The compositions of this invention may also be used to deliver buffering agents to adjust the pH of the membranes in order to promote healthy environments. From about 2 to about 20% contraceptives may be present in the compositions of this invention. From about 1 to about 10% antifungal agents may be used; from about 0.5% to about 10% antibacterial compounds buffer system may preferably be used.

The compositions of this invention may be prepared conventionally, or they may be prepared in accordance with the method of preparation of this invention. Conventional preparation consists of dissolving water soluble components such as glycerin, propylene glycol, sorbitol, inorganic base (e.g., alkali metal hydroxides), methylparaben, benzoic acid and other preservatives in water and then adding and dissolving the cellulose gum. Another conventional method of preparation consists of mixing all the ingredients into a slurry without water, and then adding the slurry to water. These methods were intended to achieve the dissolution of cellulose gum without forming lumps.

However, the method of preparation according to this invention is preferable to the previously known procedures. Glycerin and propylene glycol are mixed together first, and methylparaben and benzoic acid added to this mixture. The components are dissolved into a clear solution. To this solution is added hydroxyethylcellulose and the resulting combination mixed to obtain a slurry. Water is then added to the slurry in the same container and the contents are mixed to obtain a clear gel or solution. This procedure not only saves times by yielding a gel in a very short period of time, but saves energy by utilizing only one container during the course of the process.

The following examples serve to illustrate the compositions and methods of this invention. However, they are not presented in order to limit the scope of the invention in any way.

EXAMPLE 1

A composition in accordance with this invention was made by adding glycerin to propylene glycol in the weight percentages set forth below. The glycerin and propylene glycol are mixed together and sorbitol solution, methylparaben and benzoic acid added to the glycerin/propylene glycol mixture. The mixture is dissolved to a clear solution. Hydroxyethylcellulose is added with sodium hydroxide and the combination is mixed to obtain a slurry. Purified water is added and, within fifteen to thirty minutes, the combination forms a clear gel.

| Ingredients | % w/w |
|---|---|
| Glycerin | 30.000 |
| Propylene Glycol | 5.000 |
| Sorbitol Solution | 10.000 |
| Methylparaben | 0.200 |
| Benzoic Acid | 0.200 |
| Hydroxyethylcellulose | 0.450 |
| Sodium Hydroxide | 0.015 |
| Purified Water | 54.135 |

EXAMPLE 2

A composition in accordance with this invention was made using the method set forth in Example 1. The composition had the following components:

| Ingredients | % w/w |
|---|---|
| Glycerin | 10.000 |
| Propylene Glycol | 25.000 |
| Sorbitol Solution | 5.000 |
| Methylparaben | 0.200 |
| Benzoic Acid | 0.200 |
| Hydroxyethylcellulose | 0.520 |
| Sodium Hydroxide | 0.015 |
| Purified Water | 57.065 |

EXAMPLE 3

A method was developed to determine the degree of lubricity achieved by the compositions of this invention and to compare them with the lubricity measurements of known personal lubricant compositions. Certain devices are available that can measure the cohesive force between two surfaces. One such device is the Chatillon Digital Force Gauge. This device can measure the force required to move one surface over another surface, the force pressing the two surfaces together, also known as the kinetic coefficient of friction, can be calculated using the following equation:

$$\mu_K = F/W$$

F represents the force required to move one surface over the other, W is the force pressing the two surfaces together and $\mu_K$ is the kinetic coefficient of friction. A Chatillon Digital Force Gauge is depicted in FIG. 1. A metal disc and a glass plate are utilized as the two surfaces to be moved across one another. A thin film of the lubricant samples is applied between the two surfaces. The metal plate is attached to the Chatillon Digital Force Gauge, Model TCM 200, through a pulley. The pulley enables the metal disc to slide over the glass plate. The force gauge readings in grams are recorded every 5 seconds for 30 seconds. The coefficient of friction of this sample is calculated by dividing the force gauge reading (F) by the weight of the metal disc (W), which is the force pressing the two surfaces together.

The coefficient of friction is indirectly proportional to the lubricity of the sample tested, i.e., the lower the coefficient of friction, the higher the lubricity of the sample.

Figure 2:
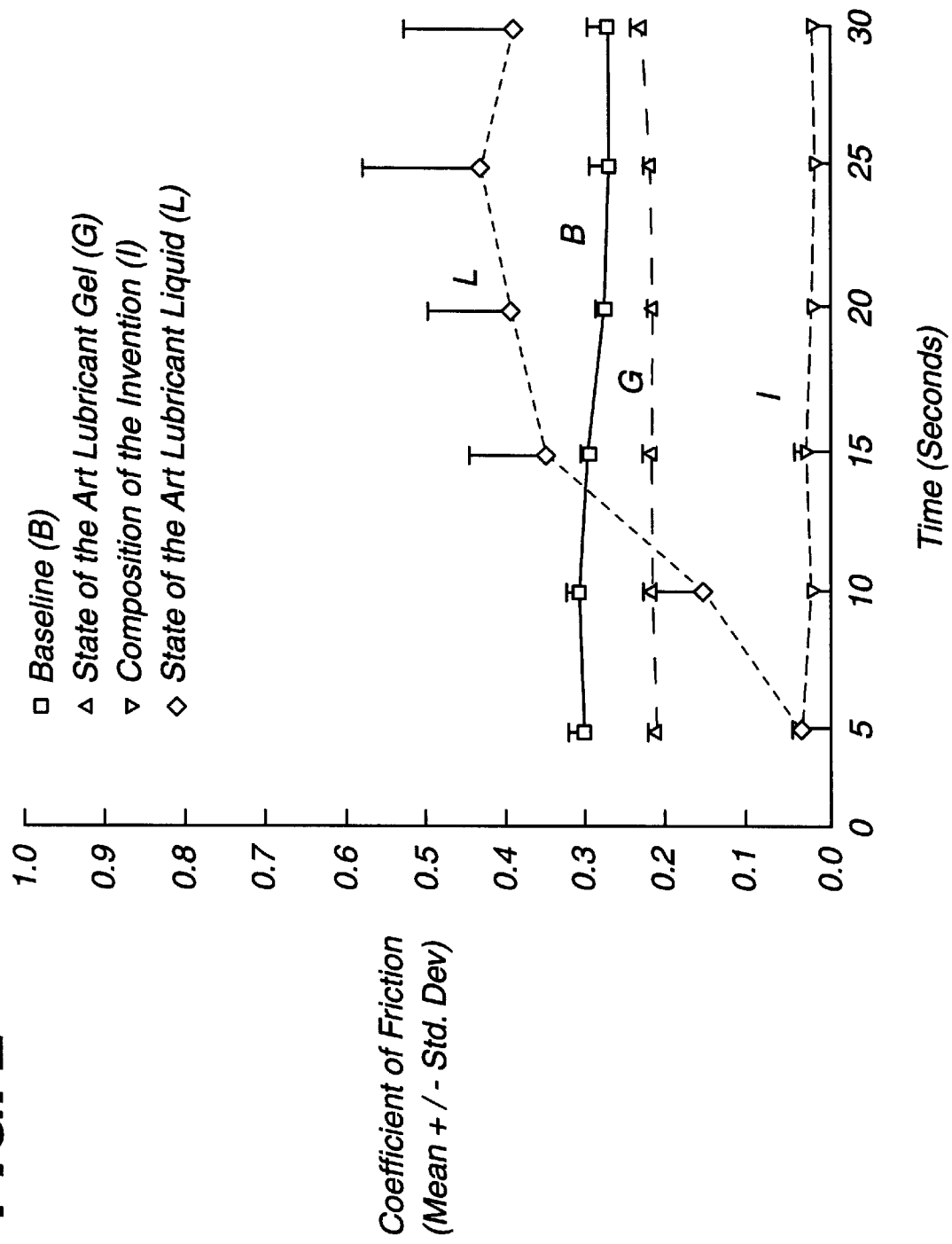
FIG. 2 is a graph depicting the coefficients of friction of a number of test samples, including a composition in accordance with this invention.

Measurements were made of the coefficients of friction of commercial lubricant gels and liquids, as well as that of compositions of this invention, using the method described above. A commercial lubricant gel (KY* Brand Lubricant Jelly), a commercial lubricant liquid (ASTROGLIDE), a baseline (test of the coefficient of friction without any product placed between the plates) were tested, as well as a composition according to this invention (formulation of Example 1). The results of the tests are set forth in Table 1 below and are graphically depicted in FIG. 2. The data show that the composition of this invention has a coefficient of friction ten to fourteen times lower than that of the baseline, seven to ten times lower than the commercial lubricant gel and three to eighteen times lower than the commercial liquid lubricant. Therefore, the composition of this invention demonstrates considerably higher lubricity than that of previously known products.

TABLE 1

Average Coefficient of Friction (Mean + Std. Dev.) vs. Time

| Time | Baseline | Lubricant Gel | Composition of the Invention | Lubricant Liquid |
|---|---|---|---|---|
| 5  | 0.302 ± 0.019 | 0.211 ± 0.011 | 0.029 ± 0.007 | 0.033 ± 0.011 |
| 10 | 0.310 ± 0.015 | 0.219 ± 0.010 | 0.022 ± 0.001 | 0.155 ± 0.060 |
| 15 | 0.300 ± 0.009 | 0.221 ± 0.011 | 0.031 ± 0.014 | 0.353 ± 0.096 |
| 20 | 0.280 ± 0.012 | 0.220 ± 0.006 | 0.024 ± 0.003 | 0.397 ± 0.103 |
| 25 | 0.274 ± 0.025 | 0.223 ± 0.007 | 0.021 ± 0.001 | 0.433 ± 0.148 |
| 30 | 0.275 ± 0.025 | 0.232 ± 0.014 | 0.022 ± 0.004 | 0.392 ± 0.137 |

What is claimed is:

1. A composition for lubricating mucous membranes comprising about 30% glycerin, about 5% propylene glycol, about 10% sorbitol, about 0.4% preservative, about 0.4% hydroxyethyicellulose, about ,0.01% sodium hydroxide and about 50% water wherein said composition has a lubricity of 33 to about 466.

2. A method of making a lubricant composition comprising:
   a) first mixing polyhydric alcohols;
   b) then adding preservatives to said polyhydric alcohols in the same container;
   c) then adding to the container a water-soluble polymer derived from cellulose and mixing the composition until it becomes a slurry; and
   d) adding water and mixing.

3. A composition for lubricating mucous membranes comprising from about 5 to about 50% by weight of glycerin, from about 2 to about 40% by weight of propylene glycol, from about 5 to about 25% by weight of sorbitol, from about 0.25 to about 1% by weight of said water-soluble cellulose gum, said composition having a pH from about 4 to about 5 and wherein said composition has a lubricity of 33 to about 466.

* * * * *

UNITED STATES PATENT AND TRADEMARK OFFICE
CERTIFICATE OF CORRECTION

PATENT NO. : 5,885,591
DATED : March 23, 1999
INVENTOR(S) : Nawaz Ahmad, Gregory E, Koll, Shun Y. Lin
Robinton Toddywala, Lorraine Wearley It is certified that error appears in the above-indentified patent and that said Letters Patent is hereby corrected as shown below:

Claim 1 , Column 5, line 18: ",0.01%" should read

-- 0.01% --

Signed and Sealed this

Thirty-first Day of August, 1999

Attest:

Q. TODD DICKINSON

*Attesting Officer*     *Acting Commissioner of Patents and Trademarks*